United States Patent [19]

Miller et al.

[11] Patent Number: 5,387,681
[45] Date of Patent: Feb. 7, 1995

[54] SYNTHESIS OF BICYCLIC AROMATIC SULFONIC ACIDS SULFONYL CHLORIDES AND SULFONAMIDES

[75] Inventors: William D. Miller, Indianapolis; Eddie V. P. Tao, Carmel, both of Ind.

[73] Assignee: Eli Lilly and Company, Indianapolis, Ind.

[21] Appl. No.: 932,404

[22] Filed: Aug. 19, 1992

[51] Int. Cl.$^6$ .......................................... C07D 233/04
[52] U.S. Cl. .................................. 544/106; 508/718; 549/350; 549/429
[58] Field of Search ................ 549/350, 429; 544/106; 548/718

[56] References Cited

U.S. PATENT DOCUMENTS

| 4,560,771 | 12/1985 | Fory | 549/467 |
| 4,659,709 | 4/1987 | Harada et al. | 549/304 |
| 4,918,206 | 4/1990 | Harada et al. | 549/468 |

FOREIGN PATENT DOCUMENTS

254577A1 1/1988
987453 3/1965 United Kingdom .

OTHER PUBLICATIONS

Kurzer, *Chemical Reviews*, 50:1–19 (1952).
Shah, et al., *Journal of Medicinal Chemistry*, 12:938 (1969).
Kittila, *Dimethylformamide Chemical Uses*, E. I. DuPont DeNemour and Co., 76, 77 (1967).
Breuer, et al., *Chimie Therapeutique*, 659 (1979).
Marshall, et al., *Journal of Organic Chemistry*, 23:927 (1958).
Marshall, et al., *Journal of Medicinal Chemistry*, 6:60 (1963).

*Primary Examiner*—C. Warren Ivy
*Assistant Examiner*—Raymond Covington
*Attorney, Agent, or Firm*—Paul J. Gaylo

[57] ABSTRACT

This invention provides a novel process for the synthesis of bicyclic aromatic sulfonic acids employing reacting a bicyclic aromatic compound with sulfur trioxide-N,N-dimethylformamide complex in the presence of a water miscible, non-reactive solvent. The resulting sulfonic acid may be converted into the corresponding sulfonyl halide by the reaction with a thionyl halide. This invention further provides a novel process for the synthesis of bicyclic aromatic sulfonamides employing the reaction conditions described supra followed by an ammonolysis or amination.

16 Claims, No Drawings

SYNTHESIS OF BICYCLIC AROMATIC SULFONIC ACIDS SULFONYL CHLORIDES AND SULFONAMIDES

BACKGROUND OF THE INVENTION

Many aromatic sulfonylureas of Formula I

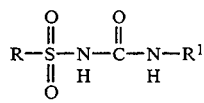

wherein R is a monocyclic or bicyclic aryl radical and $R^1$ is an organic radical, are well known in the art. Certain of these compounds are known to have hypoglycemic activities, and have been used medicinally as such agents. In addition, sulfonylureas have been taught to have herbicidal and antimycotic activities. General reviews of compounds of this structural type are taught by Kurzer, *Chemical Reviews*, 50:1 (1952) and C. R. Kahn and Y. Shechter, *Goodman and Gilman's, The Pharmacological Basis of Therapeutics*, (Gilman, et al., 8th ed. 1990) 1484–1487.

Some diarylsulfonylureas, including bicyclic aromatic sulfonylureas, have been reported as being active antitumor agents. e.g., U.S. Pat. No. 4,845,128 of Harper, et al. (1989); U.S. Pat. No. 5,110,830 of Harper, et al., issued May 5, 1992; U.S. Pat. No. 5,116,874 of G. A. Poore, issued May 26, 1992; European Patent Publication 0467613 (published Jan. 22, 1992); Grindey, et al., *American Association of Cancer Research*, 27:277 (1986); and Houghton, et al., *Cancer Chemotherapy and Pharmacology*, 25:84–88 (1989).

One commonly used synthesis for the preparation of the sulfonylureas of Formula I involves reacting an aryl sulfonamide of Formula II

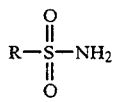

with an isocyanate of Formula III

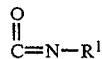

wherein R and $R^1$ are as defined supra.

In many cases the required sulfonamide is not commercially available and must be synthesized. Such compounds are routinely prepared by synthesizing the corresponding sulfonyl chloride derivative, followed by ammonolysis with ammonium hydroxide or ammonia.

Several methods of synthesizing sulfonyl chlorides are taught in the art. Shah, et al., *Journal of Medicinal Chemistry*, 12:938 (1969) describe a procedure for preparing sulfonyl chlorides known as the Meerwein Procedure. The Meerwein Procedure involves diazotization of an aniline, followed by reaction with a solution of cupric chloride, concentrated hydrochloric acid, and sulfur dioxide in glacial acetic acid.

Kittila teaches that an N,N-dimethylformamide-sulfuryl chloride adduct reacts with anisole to form paramethoxybenzene sulfonyl chloride. *Dimethylformamide Chemical Uses*, E. I. DuPont DeNemour and Co., 76, 77 (1967). Two methods for synthesizing bicyclic aromatic sulfonyl chlorides are described by Breuer and co-workers in *Chimie Therapeutique*, 659 (1979). One method involves a high temperature sulfonation of the bicyclic aromatic compound using hydrogen sulfate, followed by chlorination of the intermediate sulfonic acid. The second method teaches a low temperature chlorosulfonation employing chlorosulfonic acid to both sulfonate and chlorinate.

One synthetic route described by others utilizes the diazonium salt of 3-amino-4-(β-chloroethyl)benzene sulfonamide to directly produce dihydrobenzofuran-6-sulfonamide without forming the sulfonyl chloride intermediate. Breuer, et al., *Chimie Therapeutique*, 659 (1979)

A process described by J. A. Aikins and E. V. P. Tao teaches the reaction of an oxygen-containing bicyclic aromatic compound with a Vilsmeier reagent of Formula IV

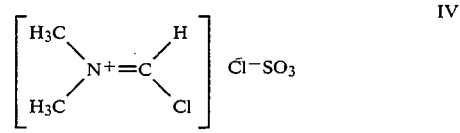

to produce sulfonyl chlorides. J. A. Aikins and E. V. P. Tao, European Patent Publication 254,577, published Jan. 27, 1988.

The major drawback with all of these methods for producing bicyclic aromatic sulfonyl chlorides and bicyclic aromatic sulfonamides is that they produce relatively low yields of useful product. The present invention describes a process for the high efficiency synthesis of these sulfonyl halides and sulfonamides.

SUMMARY OF THE INVENTION

This invention provides a process for efficiently preparing a bicyclic aromatic sulfonic acid of Formula V

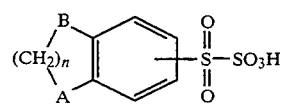

wherein:
B is —O— or —$CH_2$—;
A is —O—, —$CH_2$—, or —N($CH_3$)—; and
n is 1 or 2;
provided at least one of A or B is —O—,
which comprises reacting a compound of Formula VI

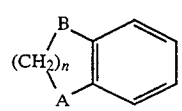

with sulfur trioxide-N,N-dimethylformamide complex in the presence of a water miscible, non-reactive solvent at a temperature of from about 30° C. to about 120° C.

In a second embodiment this invention provides a process for efficiently preparing a bicyclic aromatic sulfonyl halide of Formula VII

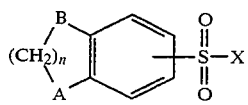

wherein:
B is —O— or —CH$_2$—;
A is —O—, —CH$_2$—, or —N(CH$_3$)—;
X is halo; and
n is 1 or 2;
provided at least one of A or B is —O—,
which comprises reacting a compound of Formula VI

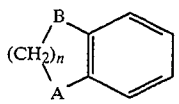

with sulfur trioxide-N,N-dimethylformamide complex in the presence of a water miscible, non-reactive solvent at a temperature of from about 30° C. to about 120° C., followed by the addition of a thionyl halide at a temperature of from about 30° C. to about 120° C.

In another embodiment, this invention provides a process for efficiently preparing a bicyclic aromatic sulfonamide of Formula VIII

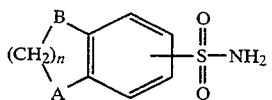

wherein:
B is —O— or —CH$_2$—;
A is —O—, —CH$_2$—, or —N(CH$_3$)—; and
n is 1 or 2;
provided at least one of A or B is —O—,
which comprises reacting a compound of Formula VI

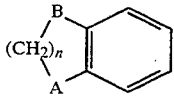

with sulfur trioxide-N,N-dimethylformamide complex in the presence of a water miscible, non-reactive solvent at a temperature of from about 30° C. to about 120° C., followed by the addition of thionyl halide at a temperature of from about 30° C. to about 120° C. followed by an ammonolysis or amination reaction.

DETAILED DESCRIPTION OF THE INVENTION

The present invention describes a process for preparing certain bicyclic aromatic sulfonic acids, sulfonyl halides and sulfonamides which are useful as intermediates in the formation of sulfonylureas. In the process of the invention, a bicyclic aromatic compound is first reacted with a sulfur trioxide-N,N-dimethylformamide complex to produce the corresponding sulfonic acid. The reaction of these two compounds is accomplished in the presence of a water miscible, non-reactive solvent, with N,N-dimethylformamide, and 1,2-dichloroethane being especially preferred.

The bicyclic aromatic compound and the sulfur trioxide-N,N-dimethylformamide complex are generally reacted in approximately equimolar quantities, but a slight excess (up to about twenty-five percent) of the sulfur trioxide-N,N-dimethylformamide complex may be employed. This reaction is generally performed at temperatures of from about 30° C. to about 120° C., with the most desired temperature range being about 50° C. to about 85° C. The reaction is generally substantially complete after 1–2 hours but longer reaction periods may be used.

In one embodiment of this invention, upon completion of the first step of this reaction, a thionyl halide is slowly added to the reaction mixture. While thionyl chloride is the most preferred, other thionyl halides, such as thionyl bromide, may be used to produce the corresponding bicyclic aromatic sulfonyl halide. The thionyl halide is added in approximately equimolar amounts. The reaction of the thionyl halide with the bicyclic aromatic sulfonic acid is performed at temperatures of from about 30° C. to about 120° C., with the preferred temperature range being from about 50° C. to about 85° C. The reaction is generally substantially complete after one hour, but it may be allowed to proceed longer, if desired.

The resulting sulfonyl halide can be isolated, if desired, but need not be, and is readily converted to a sulfonamide by ammonolysis with ammonium hydroxide or ammonia according to well known techniques. Other means of amination which are well known in the art may be used to convert the sulfonyl halide to the corresponding sulfonamide. Purification of the resulting sulfonamide is accomplished using standard techniques such as recrystallization and chromatography.

The starting materials used in the process of this invention are commercially available, known in the literature, or can be prepared by methods known in the art.

The most preferred compounds which can be made by the processes of this invention are: when n is 1, 1,3-benzodioxole-5-sulfonyl chloride, 1,3-benzodioxole-5-sulfonamide, 2,3-dihydrobenzofuran-5-sulfonyl chloride, and 2,3-dihydrobenzofuran-5-sulfonamide; and when n is 2, 1,4-benzodioxan- 6-sulfonyl chloride and 1,4-benzodioxan-6 -sulfonamide.

The terms and abbreviations used in the instant examples have their normal meanings unless otherwise designated. For example, "°C" refers to degrees Celsius; "mmoles" means millimoles; "g" refers to gram; "ml" means milliliter; "M" refers to molar or molarity; and "FDMS" refers to field desorption mass spectroscopy.

The following examples further illustrate the process of this invention. The examples are illustrative only and are not intended to limit the scope of the invention in any way.

EXAMPLE 1

Preparation of 2,3-dihydrobenzofuran-5-sulfonyl chloride

To a 250 ml, 3-neck flask under nitrogen purge was added 9.2 grams (60 mmoles) of sulfur trioxide-N,N-dimethylformamide complex and 20 ml of 1,2-dichloroethane. The slurry was stirred at room temperature and 2,3-dihydrobenzofuran (6.0 g, 50 mmoles) was added dropwise at room temperature. The slurry was slowly heated to 85° C. and aliquots were monitored for the progress of the reaction. After one hour the reaction was complete.

The reaction slurry was allowed to come to room temperature, at which time thionyl chloride (7.2 g, 60 mmoles) was added dropwise. The reaction mixture was slowly heated over the course of one hour, by which time it had reached 75° C. The mixture was allowed to cool to room temperature. Water (100 ml) was then added to the slurry.

The aqueous layer was extracted with 1,2-dichloroethane (3×25 ml). The 1,2-dichloroethane layers were combined and washed with water (25 ml) and dried over magnesium sulfate. The magnesium sulfate was filtered and washed with 1,2-dichloroethane. The 1,2-dichloroethane was removed under vacuum to give 11 grams of the title compound (>99% yield). Nuclear magnetic resonance assays confirmed the identity of the title compound. FDMS (MeOH) m/e 218 (M+).

Analysis for $C_8H_7ClO_3S$: Theory: C, 43.94; H, 3.23. Found: C, 44.13; H, 3.34.

EXAMPLE 2

Preparation of 1,4-benzodioxan-6- sulfonyl chloride

Under nitrogen purge in a 250 ml, 3-necked flask, sulfur trioxide-N,N-dimethylformamide complex (9.2 g, 60 moles) and 1,2-dichloroethane (20 ml) were mixed together. The slurry was stirred at room temperature and then 1,3-benzodioxole (6.8 g, 50 mmoles) was added dropwise.

The slurry was then slowly heated to 80° C., at which temperature, the slurry becomes more of a solution. The solution was maintained at this temperature for about 5 hours, after which it was cooled down to 60° C.

Thionyl chloride (7.2 g, 60 moles) was added dropwise to the reaction solution, causing the temperature to drop from 60° C. to 17° C. The reaction mixture was slowly heated to 75°–80 ° C., and was maintained at this temperature range for 2 hours and 15 minutes. The reaction mixture was then cooled to 60° C.

Water (100 ml) was then added and the layers separated. The aqueous layer was extracted with 1,2-dichloroethane (3×25 ml). The combined 1,2-dichloroethane layers were washed with water (25 ml ) and dried over magnesium sulfate. The water layer was extracted with 10 ml of 1,2-dichloroethane with the organic layer being added to the other 1,2-dichloroethane layers.

The magnesium sulfate was filtered and washed with 1,2-dichloroethane. The 1,2-dichloroethane was removed under vacuum to give 11.8 grams of the solid title compound (>99% yield). Nuclear magnetic resonance assays confirmed the identity of the title compound. FDMS (MeOH) m/e 234 (M+).

Analysis for $C_8H_7ClO_4S$: Theory: C, 40.95; H, 3.01. Found: C, 41.21; H, 3.07.

EXAMPLE 3

Preparation of 1,3-benzodioxole-5-sulfonyl chloride

Sulfur trioxide-N,N-dimethylformamide complex (9.2 g, 60 mmoles) and 1,2-dichloroethane (20 ml) were added to a 250 ml, 3-necked flask under nitrogen purge. The slurry was stirred at room temperature and 1,3-benzodioxole was added dropwise at room temperature. The slurry was slowly heated to 74° C. and was maintained at that temperature for about 8 hours.

The reaction mixture was cooled to room temperature and allowed to stir overnight at room temperature. Thionyl chloride (7.2 g, 60 mmoles) was added dropwise. The reaction mixture was slowly heated to 74° C. and was maintained at that temperature for 4.5 hours.

The reaction mixture was then cooled to room temperature. water (100 ml) was then added and the layers separated. The aqueous layer was extracted with 1,2-dichloroethane (3×25 ml). The combined 1,2-dichloroethane layers were washed with water (25 ml) and dried over magnesium sulfate. The magnesium sulfate was filtered and washed with 1,2-dichloroethane. The 1,2-dichloroethane was removed under vacuum leaving a liquid which solidified at room temperature.

The last traces of N,N-dimethylformamide were removed by dissolving the solid in ethyl acetate and washing thrice with water. The ethyl acetate layer was dried over magnesium sulfate, which was removed by filtration, leaving 7.8 g (71% yield) of the title compound. Nuclear magnetic resonance assays confirmed the identity of the title compound. FDMS (MeOH) m/e 220 (M+).

Analysis for $C_7H_5ClO_4S$: Theory: C, 38.11; H, 2.28. Found: C, 38.30; H, 2.27.

EXAMPLE 4

Preparation of 2,3-dihydrobenzofuran-5-sulfonyl chloride

Sulfur trioxide-N,N-dimethylformamide complex (9.2 g, 60 mmoles) and N,N-dimethylformamide (20 ml) were added to a 250 ml, 3-necked flask under nitrogen purge. The solution was stirred at room temperature and 2,3-dihydrobenzofuran (6.0 g, 50 mmoles) was added dropwise.

The solution was slowly heated to 85°–90° C. over the course of one hour. The light brown solution was allowed to come to room temperature and thionyl chloride (7.2 g, 60 mmoles) was added dropwise. The mixture was allowed to stir one hour at room temperature.

The solution was slowly heated to 85° C. and was maintained at that temperature for 1 hour. The solution was allowed to cool to 40° C. Toluene (25 ml) was added to the solution, which was then poured into a mixture of ice and water (50 ml). Another 25 ml aliquot of toluene was added. The mixture was stirred for 10 minutes to dissolve any solids and the layers were separated.

The aqueous layer was extracted with toluene (3×25 ml). The combined toluene layers were washed with water and dried over magnesium sulfate. The magnesium sulfate was removed and washed with toluene. The toluene was removed under vacuum, leaving 10.0 g of the title product (91.7% yield). Nuclear magnetic resonance assays confirmed the identity of the title compound. FDMS (MeOH) m/e 218 (M+).

Analysis for $C_8H_7ClO_3S$: Theory: C, 43.94; H, 3.23. Found: C, 44.14; H, 3.24.

EXAMPLE 5

Preparation of 2,3-dihydrobenzofuran-5-sulfonamide

Into a 250 ml, 3-necked flask under nitrogen purge were added sulfur trioxide-N,N-dimethylformamide complex (9.2 g, 60 mmoles) and 1,2-dichloroethane (20 ml). The slurry was stirred at room temperature and 2,3-dihydrobenzofuran (6.0 g, 50 mmoles) was added dropwise at room temperature. The purple slurry was slowly heated to 85° C. over the course of one hour. The progress of the reaction was monitored using thin layer chromatography.

Once the reaction was completed, the reaction mixture was allowed to cool to room temperature and thionyl chloride (7.2 g, 60 mmoles) was added dropwise. The reaction mixture was slowly heated to 75° C. and maintained at that temperature until the reaction had completed, as determined by thin layer chromatography.

The reaction mixture was allowed to cool to room temperature and water (100 ml) was added. The aqueous layer was collected and extracted with 1,2-dichloroethane (3×25 ml). The combined 1,2-dichloroethane layers were washed with water (25 ml) and dried over magnesium sulfate. The magnesium sulfate was filtered and washed with 1,2-dichloroethane.

This 1,2-dichloroethane solution containing the desired sulfonyl chloride was added to a solution of 1,2-dichloroethane (20 ml) and gaseous ammonia (14.7 g) cooled by a dry ice/acetone bath. This reaction was allowed to stir overnight, eventually coming to room temperature.

The precipitate was filtered and washed with 1,2-dichloroethane, followed by a wash with water and, finally, a wash with ether. The precipitate was vacuum dried to give 6.9 g of the title product. The 1,2-dichloroethane filtrate was evaporated under vacuum to give 2.0 g of solid with was slurried with 25 ml of water. This precipitate was filtered and washed with water and ether, the ether being removed by vacuum-drying. The 1.2 g of solid title compound recovered by this extraction of the filtrate (Sample B), when combined with the 6.9 g of title compound in the earlier precipitate (Sample A) results in an overall 81% yield of the title compound. Nuclear magnetic resonance assays confirmed the identity of the title compound.

Analysis for $C_8H_9NO_3S$: Sample A FDMS (MeOH) MeOH m/e 199 (M+). Theory: C, 48,23; H, 4.55; N, 7.03. Found: C, 48.33; H, 4.47; N, 6.96. Sample B FDMS (MeOH) m/e 199 (M+). Theory: C, 48,23; H, 4.55; N, 7.03. Found: C, 48.33; H, 4.49; N, 7.01.

We claim:

1. A process for preparing a bicyclic aromatic sulfonyl halide of the formula

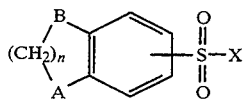

wherein:
X is halo;
B is —O— or —CH$_2$—;
A is —O—, —CH$_2$—, or —N(CH$_3$)—; and
n is 1 or 2;
provided at least one of A or B is —O—,
which comprises reacting a compound of the formula

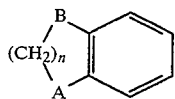

with sulfur trioxide-N,N-dimethylformamide complex in the presence of a water miscible, non-reactive solvent at a temperature of from about 30° C. to about 120° C., followed by the addition of a thionyl halide at a temperature of from about 30° C. to about 120° C.

2. The process as claimed in claim 1 wherein the thionyl halide is thionyl chloride.

3. The process as claimed in claim 1 wherein the reaction temperatures are from about 50° C. to about 85° C.

4. The process as claimed in claim 1 wherein the bicyclic aromatic sulfonyl halide is 2,3-dihydrobenzofuran-5-sulfonyl chloride.

5. The process as claimed in claim 1 wherein the bicyclic aromatic sulfonyl halide is 1,3-benzodioxole-5-sulfonyl chloride.

6. The process as claimed in claim 1 wherein the bicyclic aromatic sulfonyl halide is 1,4-benzodioxan-6-sulfonyl chloride.

7. A process for preparing a bicyclic aromatic sulfonamide of the formula

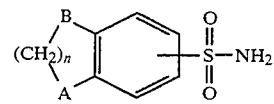

wherein:
B is —O— or —CH$_2$—;
A is —O—, —CH$_2$—, or —N(CH$_3$)—; and
n is 1 or 2;
provided at least one of A or B is —O—,
which comprises reacting a compound of the formula

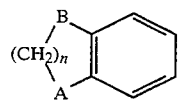

with sulfur trioxide-N,N-dimethylformamide complex in the presence of a water miscible, non-reactive solvent at a temperature of from about 30° C. to about 120° C., followed by the addition of a thionyl halide at a temperature of from about 30° C. to about 120° C. followed by an ammonolysis or amination reaction.

8. The process as claimed in claim 7 wherein the thionyl halide is thionyl chloride.

9. The process as claimed in claim 7 wherein the reaction temperatures are from about 50° C. to about 85° C.

10. The process as claimed in claim 7 wherein the bicyclic aromatic sulfonamide is 2,3-dihydrobenzofuran-5-sulfonamide.

11. The process as claimed in claim 7 wherein the bicyclic aromatic sulfonamide is 1,3-benzodioxole-5-sulfonamide.

12. The process as claimed in claim 7 wherein the bicyclic aromatic sulfonamide is 1,4-benzodioxan-6-sulfonamide.

13. A process for preparing a bicyclic aromatic sulfonic acid of the formula

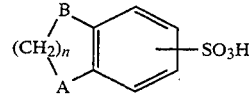

wherein:
B is —O— or —CH$_2$—;
A is —O—, —CH$_2$—, or —N(CH$_3$)—; and
n is 1 or 2;
provided at least one of A or B is —O—,
which comprises reacting a compound of the formula

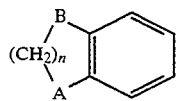

with sulfur trioxide-N,N-dimethylformamide complex in the presence of a water miscible, non-reactive solvent at a temperature of from about 30° C. to about 120° C.

14. The process as claimed in claim 13 wherein the bicyclic aromatic sulfonic acid is 2,3-dihydrobenzofuran-5-sulfonic acid.

15. The process as claimed in claim 13 wherein the bicyclic aromatic sulfonic acid is 1,3-benzodioxole-5-sulfonic acid.

16. The process as claimed in claim 13 wherein the bicyclic aromatic sulfonic acid is 1,4-benzodioxan-6-sulfonic acid.

* * * * *